United States Patent
Komp et al.

(10) Patent No.: US 11,172,184 B2
(45) Date of Patent: Nov. 9, 2021

(54) SYSTEMS AND METHODS FOR IMAGING A PATIENT

(71) Applicant: COVIDIEN LP, Mansfield, MA (US)

(72) Inventors: John W. Komp, Dillon, CO (US); Joe D. Sartor, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 16/682,801

(22) Filed: Nov. 13, 2019

(65) Prior Publication Data

US 2020/0195903 A1 Jun. 18, 2020

Related U.S. Application Data

(60) Provisional application No. 62/782,683, filed on Dec. 20, 2018, provisional application No. 62/779,229, filed on Dec. 13, 2018, provisional application No. 62/779,242, filed on Dec. 13, 2018.

(51) Int. Cl.
| | |
|---|---|
| A61B 1/00 | (2006.01) |
| A61B 34/20 | (2016.01) |
| A61B 90/30 | (2016.01) |
| H04N 13/156 | (2018.01) |
| H04N 13/25 | (2018.01) |
| H04N 5/33 | (2006.01) |

(52) U.S. Cl.
CPC ............ *H04N 13/156* (2018.05); *A61B 34/20* (2016.02); *H04N 5/33* (2013.01); *H04N 13/25* (2018.05); *A61B 2034/2057* (2016.02); *A61B 2034/2065* (2016.02)

(58) Field of Classification Search
USPC ........................................................ 348/45
See application file for complete search history.

(56) References Cited

U.S. PATENT DOCUMENTS

| | | |
|---|---|---|
| 5,687,737 A | 11/1997 | Branham et al. |
| 7,474,407 B2 | 1/2009 | Gutin |
| 7,538,859 B2 | 5/2009 | Tearney et al. |
| 7,559,895 B2 | 7/2009 | Stetten et al. |
| 7,756,305 B2 | 7/2010 | Price |
| 7,857,756 B2 | 12/2010 | Warren et al. |
| 7,949,385 B2 | 5/2011 | Khamene et al. |
| 7,952,718 B2 | 5/2011 | Li et al. |

(Continued)

FOREIGN PATENT DOCUMENTS

EP 3225151 A1 10/2017

OTHER PUBLICATIONS

European Search Report issued in European Patent Application No. EP 19215517 dated Apr. 14, 2020, 9 pages.

*Primary Examiner* — Patricia I Young
(74) *Attorney, Agent, or Firm* — Weber Rosselli & Cannon LLP

(57) ABSTRACT

Systems and methods of imaging include projecting infrared (IR) light from the endoscope toward the at least one anatomical feature (e.g., the exterior of a liver or lung), capturing the IR light, projecting optical light from the endoscope toward a similar portion of the anatomical feature, and capturing the optical light. Once the IR light and the optical light are captured, both are associated with one another to generate an intra-operative 3D image. This projection and capture of IR and optical light may occur at discrete times during the imaging process, or simultaneously.

18 Claims, 11 Drawing Sheets

(56) References Cited

U.S. PATENT DOCUMENTS

| | | |
|---|---|---|
| 8,335,557 B2 | 12/2012 | Maschke |
| 8,382,662 B2 | 2/2013 | Soper et al. |
| 8,384,909 B2 | 2/2013 | Yun et al. |
| 8,460,195 B2 | 6/2013 | Courtney et al. |
| 8,494,794 B2 | 7/2013 | Dutta et al. |
| 8,784,321 B2 | 7/2014 | Courtney et al. |
| 8,983,580 B2 | 3/2015 | Boppart et al. |
| 9,398,936 B2 | 7/2016 | Razzaque et al. |
| 9,554,774 B2 | 1/2017 | Moore et al. |
| 9,861,338 B2 | 1/2018 | Kanade et al. |
| 10,391,277 B2 | 8/2019 | Rahimian et al. |
| 2014/0336461 A1 | 11/2014 | Reiter et al. |
| 2019/0038365 A1* | 2/2019 | Soper ............ A61B 6/487 |

* cited by examiner

SYSTEMS AND METHODS FOR IMAGING A PATIENT

CROSS-REFERENCE TO RELATED APPLICATION

This application claims the benefit of U.S. Provisional Application Ser. No. 62/782,683, filed Dec. 20, 2018, and is related to, and claims the benefit of, U.S. Provisional Application Ser. No. 62/779,242, filed on Dec. 13, 2018 and U.S. Provisional Application Ser. No. 62/779,229, filed on Dec. 13, 2018, the entire contents of each of which being incorporated by reference herein.

BACKGROUND

Technical Field

The disclosure relates to imaging techniques performed in association with surgical procedures and, more particularly, to association of 2D image data with 3D image data.

Description of Related Art

Minimally-invasive surgical procedures have become both a common and effective means for diagnosing and treating a variety of medical conditions. For example, laparoscopic surgical procedures which rely on endoscopic surgical instruments allow for reduced incision length into tissue to allow access to the surgical site, as well as trauma during certain surgical procedures. Similarly, robotic surgical procedures allow clinicians to maintain the position and orientation of an endoscopic surgical instrument relative to the surgical site with minimal effort.

SUMMARY

Provided in accordance with aspects of the disclosure are systems and methods for imaging within a body of a patient. In an aspect, the method may include analyzing a first image including reflected IR light captured by an IR camera associated with an endoscope, analyzing a second image including reflected optical light captured by an optical light camera associated with the endoscope, associating the first image with the second image, and generating an intra-operative 3D image based on the association of the first image with the second image.

According to an aspect, associating the first image and the second image includes mapping the first image to the second image by translating points of the first image to corresponding points of the second image.

The method may further include projecting a plurality of IR light beams toward at least one anatomical feature of the patient. In an aspect, the plurality of light beams are projected toward the at least one anatomical feature in spaced relation relative to one another. Additionally, or alternatively, the plurality of IR light beams projected toward the at least one anatomical feature are projected in a grid pattern.

According to an aspect, the method further includes determining a plurality of 3D coordinates based on the first image.

In an aspect, the generating an intra-operative 3D image is further based on the plurality of 3D coordinates.

According to an aspect, the method may further include displaying the intra-operative 3D image on a display.

According to another aspect of the disclosure, a system for imaging within a body of a patient is provided. The system includes an endoscope and a computing device in communication with the endoscope. The endoscope includes an infrared (IR) light source configured to project a plurality of IR light beams onto at least one anatomical feature, an IR camera configured to capture a first image, an optical light source configured to project optical light onto the at least one anatomical feature, and an optical camera configured to capture a second image. The first image includes a reflection of the plurality of IR light beams and the second image includes at least one anatomical feature illuminated by the optical light source. The computing device includes a processor and a memory storing instructions thereon which, when executed by the processor, cause the computing device to associate the first image with the second image, generate an intra-operative 3D image based on the association of the first image with the second image, and display the intra-operative 3D image.

In an aspect, the computing device is configured to map the first image to the second image by translating points of the first image to corresponding points of the second image.

The plurality of IR light beams projected onto the at least one anatomical feature may define a grid pattern.

In an aspect, the computing device is configured to determine a plurality of 3D coordinates based on the first image. Additionally, or alternatively, the computing device is configured to generate the intra-operative 3D image based on the association of the first image with the second image and further based on the plurality of 3D coordinates. In an aspect, the computing device may associate the generated intra-operative 3D image with previously acquired pre-operative images.

According to an aspect, the computing device is configured to generate a 3D model based on the association of the generated intra-operative 3D image with previously acquired pre-operative images and display the generated 3D model.

In yet another aspect of the disclosure a non-transitory computer-readable storage medium is provided. The non-transitory computer-readable storage medium is encoded with a program that, when executed by a processor, causes the processor to associate a first image of at least one anatomical feature including IR light projected thereon with a second image of the at least one anatomical feature, generate an intra-operative 3D image based on the association of the first image with the second image, and associate the generated intra-operative 3D image with previously acquired pre-operative images.

In an aspect, the processor is further caused to generate a 3D model based on the association of the generated intra-operative 3D image with previously acquired pre-operative images and display the generated 3D model. Additionally, or alternatively, the processor is further caused to map the first image to the second image by translating points of the first image to corresponding points of the second image.

According to an aspect, the processor is caused to determine a plurality of 3D coordinates based on the first image. Additionally, or alternatively, the processor is caused to generate the intra-operative 3D image based on the association of the first image with the second image and further based on the plurality of 3D coordinates.

BRIEF DESCRIPTION OF THE DRAWINGS

Various aspects and features of the disclosure are described hereinbelow, with reference to the drawings, wherein.

DETAILED DESCRIPTION

Figure 1:
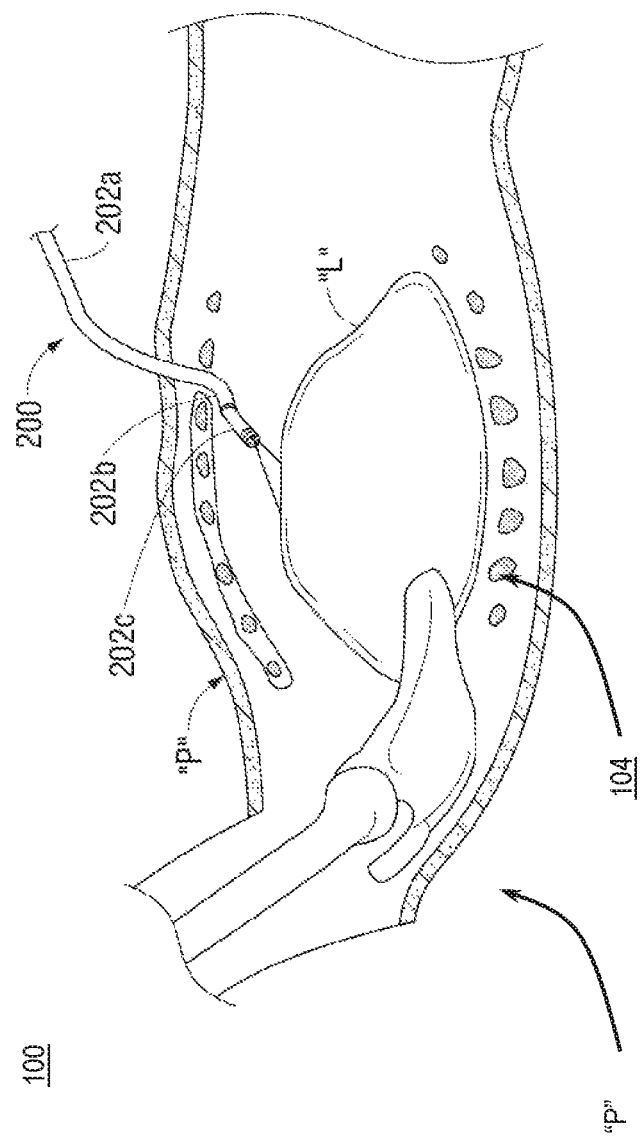
FIG. 1 is a side, cross-sectional, view of the thoracic cavity of a patient with an endoscope having surface scanning capabilities disposed partially therein, according to embodiments of the disclosure.

The disclosure relates to systems and methods for generating 3D images based on 2D image data and 3D image data collected during surgical procedures. These systems and methods are disclosed in response to the continuing need for improved images capture systems suitable for inclusion in minimally-invasive surgical procedures. In particular, there is a need for more robust systems and methods of capturing 2D and 3D images during these surgical procedures.

Systems and methods are disclosed herein for capturing and associating 2D image data and 3D image data captured within the body of a patient for later display on a 2D or 3D display device. These systems and methods generally include generating an intra-operative 3D model based on an infrared (IR) image captured either in close temporal proximity to, or simultaneously with a captured 2D image. By associating the 2D image with the intra-operative 3D model, a 3D image may be generated or rendered and displayed in conjunction with and/or in addition to other data during surgical procedures (e.g., a 3D model of the anatomy of the patient). This enables a clinician to better visualize the internal anatomic features of a patient in proximity to an endoscope or other similar surgical devices during a surgical procedure.

The systems and methods described herein may be useful in various surgical procedures in which a patient is being diagnosed and/or treated, e.g., in cavities (insufflated or otherwise established), luminous structures, etc. For example, in an embodiment in which a clinician is performing a diagnosis of targets in a thoracic area of a patient, the disclosed systems and methods may be employed to assist during navigation of an endoscope moving toward anatomical features or targets within body. Specifically, the systems and methods described enable imaging the features for later display on an intra-operative 3D model or a two-dimensional 3D rendering (where a 3D display is not available). Additionally, as will be described in further detail, the disclosed systems and methods may provide the clinician with the ability to view and/or determine various characteristics of anatomical features, structures, and targets, as well as the position of one or more surgical tools relative to the body of the patient (including the aforementioned landmarks), as well as other surgical tools disposed within or about the patient. These aspects, and others, of the disclosure are detailed hereinbelow.

Throughout this description, the term "clinician" is referred to herein as an individual who provides or assists in providing therapeutic treatments to patients such as, without limitation, doctors, surgeons, nurses, and other such support staff. The term "distal" used herein describes the portion of the subject device or component that is farther from the clinician, whereas the term "proximal" used herein describes the portion of the subject device or component that is closer to the clinician. The phrases "in an embodiment," "in embodiments," or "in other embodiments" may each refer to one or more of the same or different embodiments in accordance with the disclosure. Further, while reference may be made to elements in the singular, such distinction is intended only to simplify such description and is not intended to limit the subject matter of the disclosure. The term "target" used herein refers to tissue (either soft or hard) or areas/regions in the body of a patient that is designated as of interest for diagnosis or for therapeutic deliveries. Similarly, the term "anatomical feature" or its variants, refers to organs, tissue, vessels, or other discrete portions of the body of a patient.

FIG. 1 illustrates a cross-sectional view of a patient 100 depicted with an endoscope 200 positioned trans-thoracically therein. The endoscope 200 is configured for insertion through an opening in the patient "P", either via an incision or via an existing opening (e.g., via the mouth and/or nose of the patient (see FIG. 9)).

Figure 2:
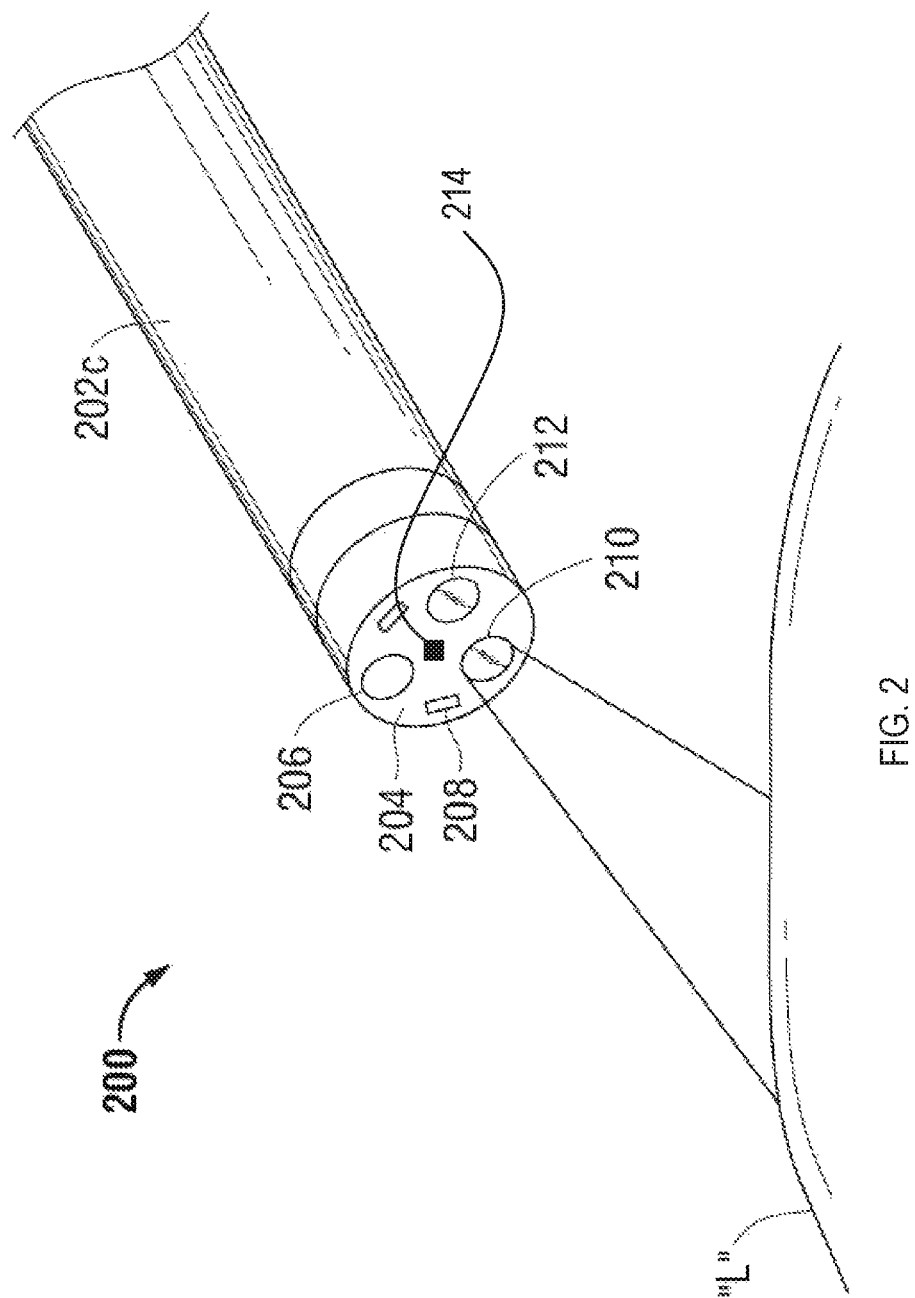
FIG. 2 is a front perspective view of a distal portion of an endoscope according to embodiments of the disclosure.

FIGS. 1 and 2 illustrate a side, cross-sectional, view of a thoracic cavity of a patient with an endoscope 200 having surface scanning capabilities disposed partially therein. While description of the endoscope 200 with respect to the environment illustrated in FIGS. 1 and 2 refers to use of the endoscope 200 without the assistance of a trocar or other such delivery system, it will be understood that the endoscope 200 may be configured to be extended through such systems. The endoscope 200 includes an elongated body 202. In embodiments, the elongated body 202 is configured to be advanced within a suitable trocar or other device capable of receiving, and subsequently delivering, endoscopes into the body (e.g., an endobronchial catheter, thoracic catheter, trocar, and the like). The elongated body 202 may include first, second, and third segments 202a, 202b, 202c, respectively, each coupled to each other and capable of being manipulated to move relative to one another. In this manner, the endoscope 200 may be positioned in close proximity or through the chest wall of the patient "P" during navigating therethrough (e.g., through ribs 104 of patient "P"). As can be appreciated, the elongated body 202 of the endoscope 200 may include any number of segments to aid in the maneuverability of the endoscope 200 within the body of the patient "P" (e.g., through the thoracic cavity or luminal structures).

The endoscope 200 includes an optical camera 206, a light source 208, a structured light projection source or structured light scanner or laser 210 (e.g., IR light source), and a second camera 212. Although generally illustrated as being disposed in a circular configuration about the distal surface 204 of the endoscope 200, it is contemplated that the optical camera 206, the light source 208, the laser 210, and/or the second camera 212 may be disposed in any suitable configuration. The optical camera 206 may be a visual-light optical camera such as a charge-coupled device (CCD), complementary metal-oxide semiconductor (CMOS), N-type metal oxide semiconductor (NMOS), or any other such suitable camera sensor known in the art. In one non-limiting embodiment, the optical camera 206 is a CCD camera having a predetermined resolution (e.g., 1080p). The endoscope 200 may also have one or more EM sensors 214 disposed about the distal portion of the endoscope 200 (e.g., the distal surface 204), or at any desired point along or within the endoscope 200, to facilitate location of the one or more EM sensors 214, and any associated components of the endoscope 200, during EM navigation. The EM sensor 214 is configured to communicate with EM tracking systems (e.g., EM tracking system 708 (see FIG. 7)).

The light source 208 is a light emitting diode (LED) configured to emit white light, although it is contemplated that any light emitting device configured to emit light along any light frequency may be utilized. The laser 210 may be any structured light scanner known in the art, such as an LED or LED infrared laser that is dispersed into a scan pattern (e.g., a line, mesh, dot matrix, etc.), by a rotating mirror, a beam splitter. In embodiments, the laser 210 is an LED laser having collimated light. The second camera 212 is a CCD camera capable of detecting. IR light, although it is contemplated that the second camera 212 may detect visible light, such as visible green light or the like, depending on the tissue or target being scanned. Specifically, visible green light contrasts with tissue having a red or pinkish hue, enabling the second camera 212 to more easily identify the topography of the tissue or target. Likewise, visible blue light that is absorbed by hemoglobin may enable the system to detect vascular structures along with a vascular topology to act as additional reference points to be matched when aligning images captured by the second camera 212. A digital filter (not explicitly shown) or filter having narrow band optical grating (not explicitly shown) may be used to inhibit extraneous visible light emitted from the laser 210, thereby limiting the light exposure of the second camera 212 from light emitted by the laser 210 at a predetermined wavelength, reducing or preventing the distraction of clinicians by such light during surgical procedures. In embodiments, the visible light is filtered from the image captured by the optical camera 206 and transmitted to the surgeon via a computing device 400 (FIG. 6) such that the image is clear and free from extraneous light patterns.

In embodiments, the second camera 212 may be any thermographic camera known in the art, such as a ferroelectric, silicon microbolometer, or uncooled focal plane array (UFPA), or may be any other suitable visible light sensor such as a CCD, CMOS, NMOS, and the like, configured to sense light transmitted by the laser 210 (e.g., as reflected). In embodiments, the distal surface 204 may include a suitable transparent protective cover (not shown) capable of inhibiting fluids and/or other contaminants from coming into contact with the optical camera 206, the light source 208, the laser 210, and/or the second camera 212. Since the distance between the laser 210 and the second camera 212 relative to the optical camera 206 is fixed (e.g., the offset of the optical camera 206 relative to the laser 210 and the second camera 212), the images obtained by the optical camera 206 can more accurately be matched with pre-operative images, as will be discussed in further detail below. It is contemplated that the various sensors disposed within or about the distal portion of the third segment 202c may be separate and distinct components with associated hardware and/or software, or may be part of a commercial platform such as the Intel® RealSense™ technology system developed by Intel.

In embodiments, the laser 210 may be disposed on an outer surface of the third segment 202c. As can be appreciated, the location of the laser 210 on the outer surface of the third segment 202c enables triangulation where the laser 210 and the second camera 212 are directed at an angle from the centerline of the third segment 202c (e.g., the laser 210 and the second camera 212 are disposed at an angle incident to a longitudinal axis defined by the third segment 202c).

Figure 3A:
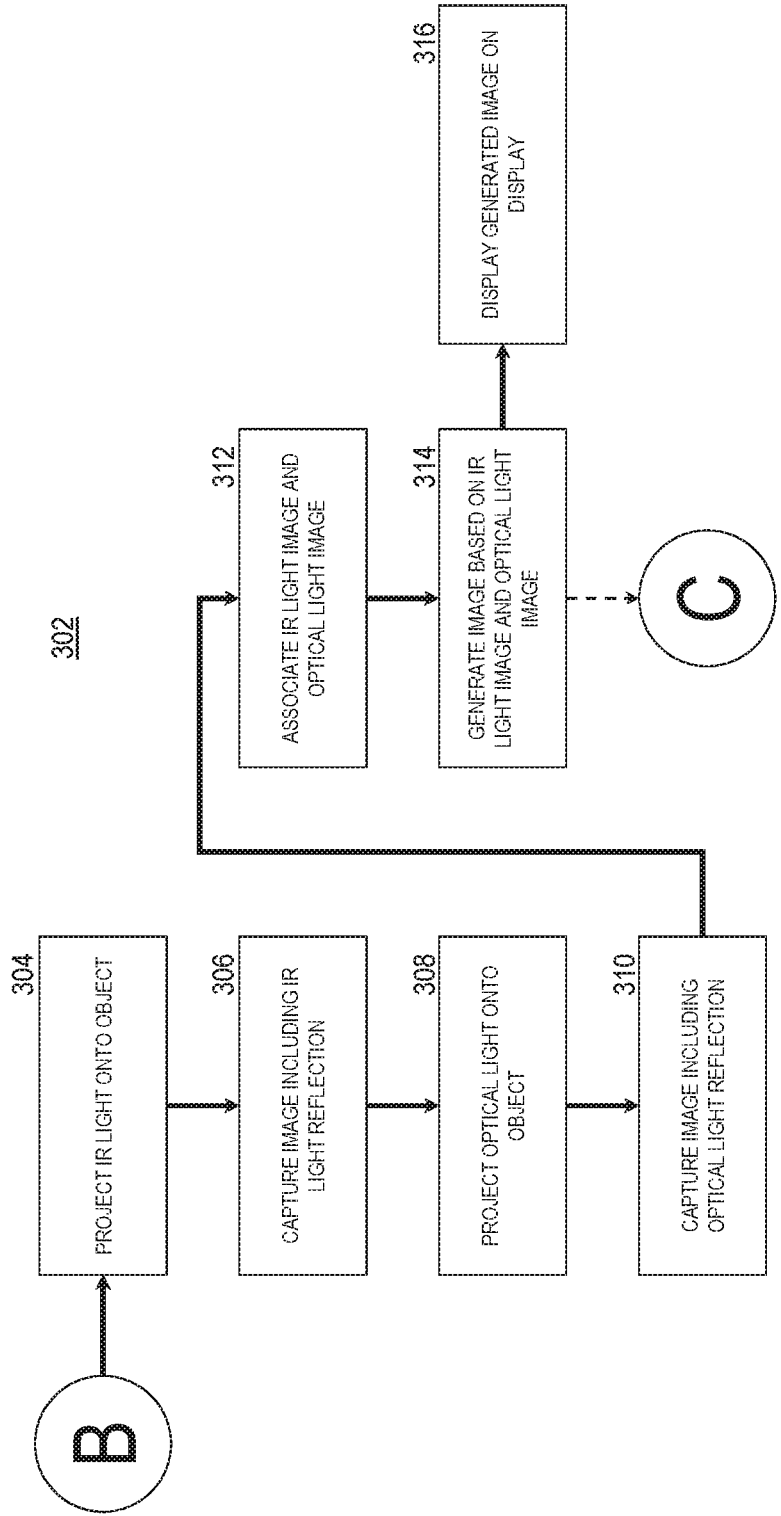
FIGS. 3A-3C are flowcharts associated with illustrative methods for performing imaging of the surgical site, according to embodiments of the disclosure.
Figure 3B:
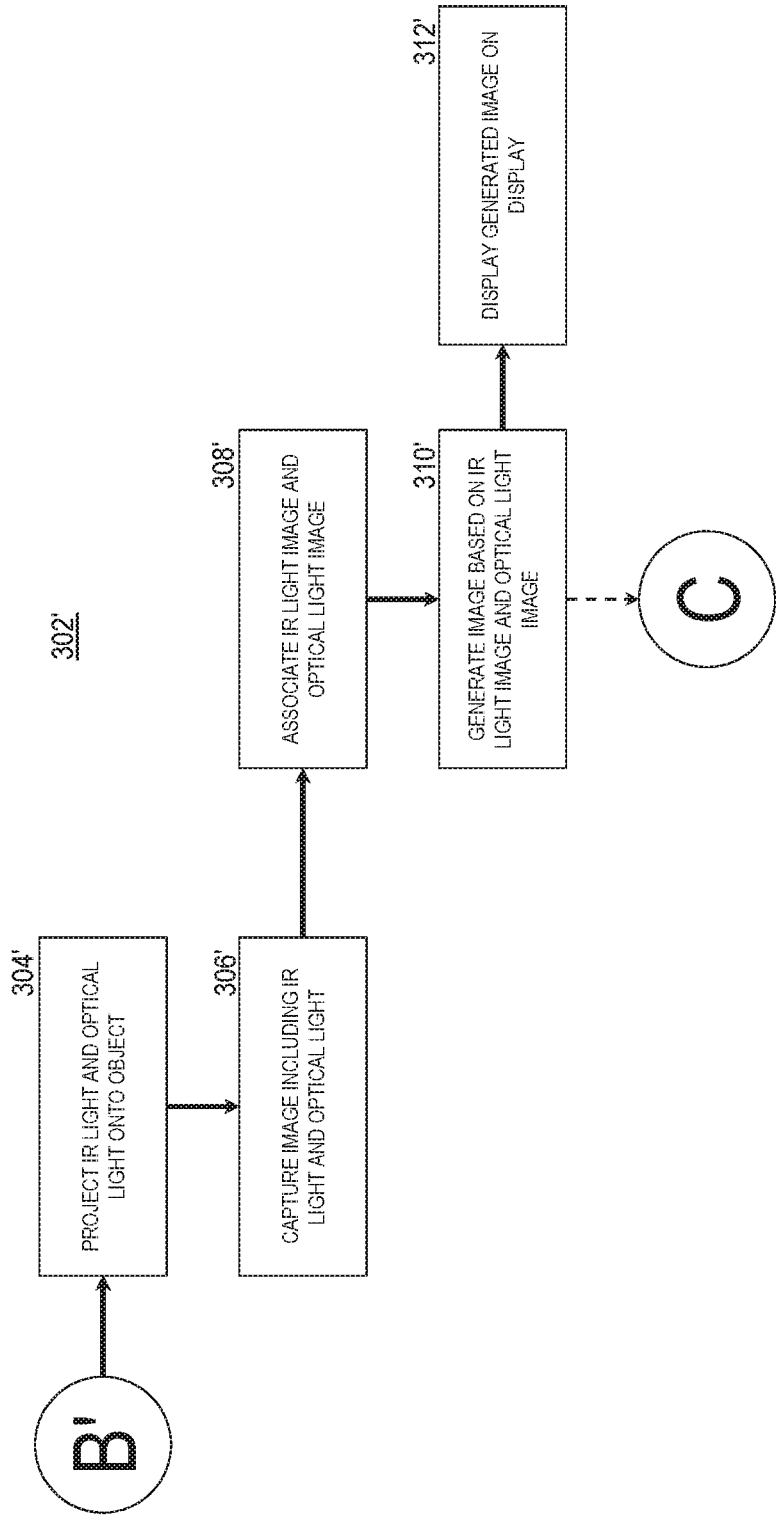
Figure 3C:
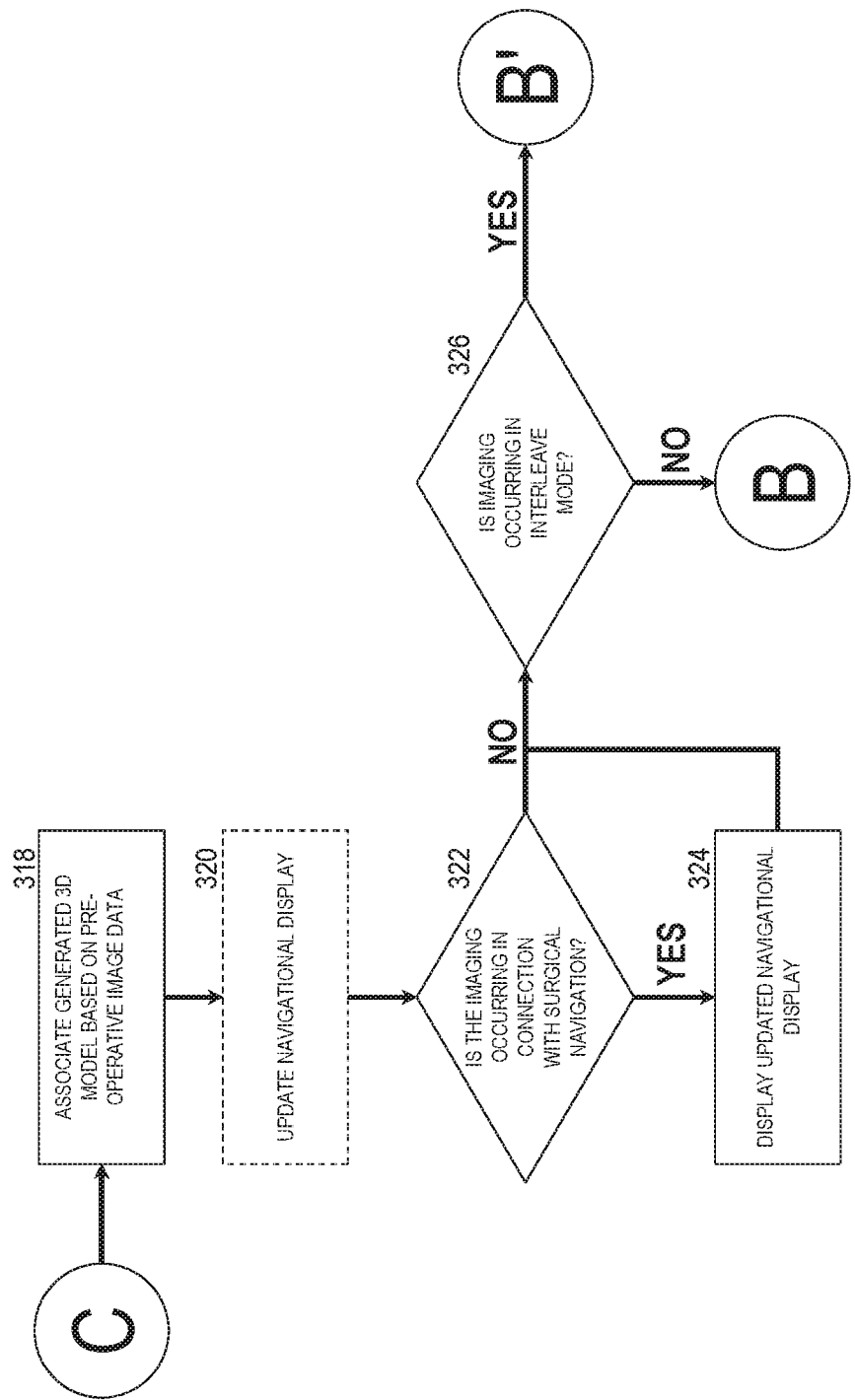
Figure 6:
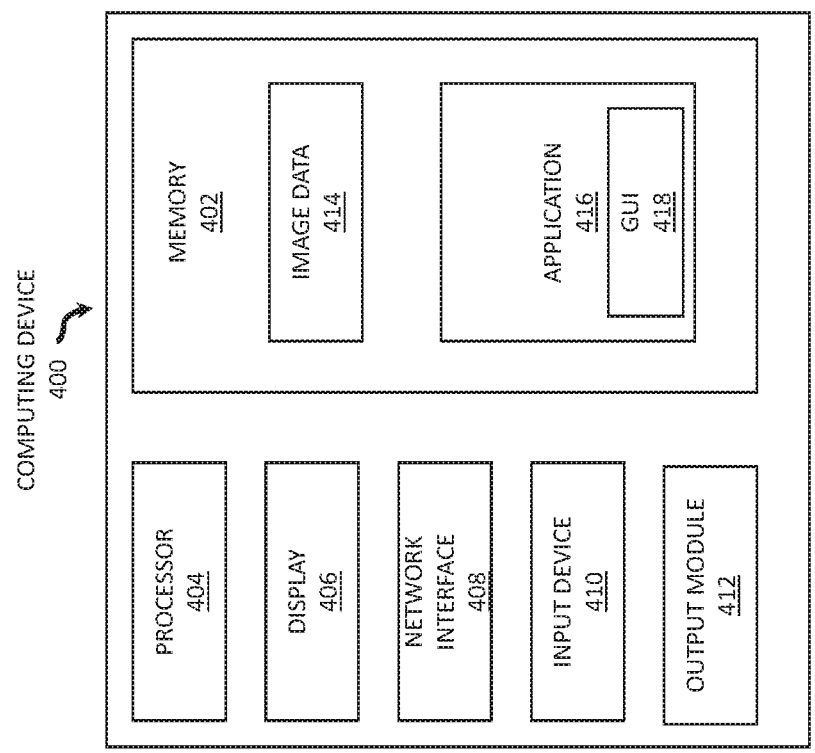
FIG. 6 is a block diagram of a computing device according to embodiments of the disclosure.
Figure 9:
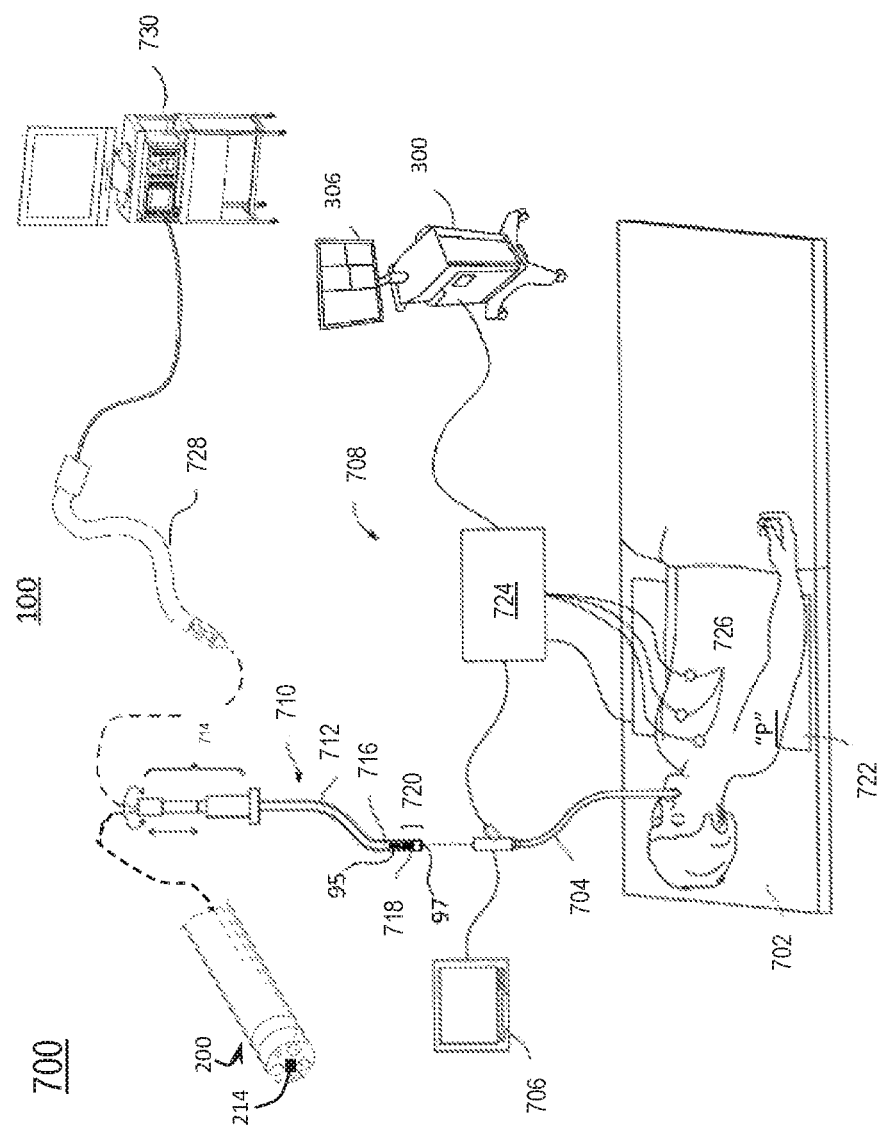
FIG. 9 is a perspective view of a surgical system according to embodiments of the disclosure.

The flowcharts illustrated in FIGS. 3A-3C outline methods of employing endoscopes (e.g., endoscope 200) to display select target tissue of a patient "F" (FIGS. 1 and 9). The methods are referred to generally as process 302. While process 302 includes various steps described in a particular sequence, it will be understood by one skilled in the art that the described steps may be performed in a different order, repeated, and/or omitted without departing from the scope of the disclosure. For example, where navigation is not desired, the endoscope 200 may be used to generate or render images and transmit data signals of the images to a display 406 for display to clinicians. Additionally, the below description of process 302 refers to various actions performed by the computing device 400, but it will be apparent to one skilled in the art that these actions may be performed on various computing devices configured to operate in a similar manner. The actions performed may also occur in response to instructions stored in one or more memories 402 which are configured for execution on the one or more processors 404 of the computing device 400 (FIG. 6).

Interleaved Intra-Operative Image Capture

As the endoscope 200 is advanced through or otherwise positioned within the body of the patient "P", the endoscope 200 performs imaging of one or more of the areas therein (process 302). As noted above, this imaging may occur independent of, or in connection with, EM navigation. More particularly, the endoscope 200 may receive 2D and/or 3D image data, generate era intra-operative 3D model and/or a 2D rendering of a 3D image (in the case where display is via a 2D display 406), and either display the generated intra-operative 3D model and/or the intra-operative image, data on a display 406 of the computing device 400 (FIG. 6). The generated intra-operative 3D model and/or the intra-operative image data may be stored in the memory 402 of the computing device 400 for later recall. In embodiments, the image data may be associated or mapped to the pre-operative 3D model generated based on the pre-operative image data of the patient "F". It will be understood that the actions performed by the endoscope 200 may be caused by executing instructions (e.g., the application 416) on the processor 404 or by a local control circuitry disposed, or otherwise in electrical communication with, the various components of the endoscope 200.

Figure 5B:
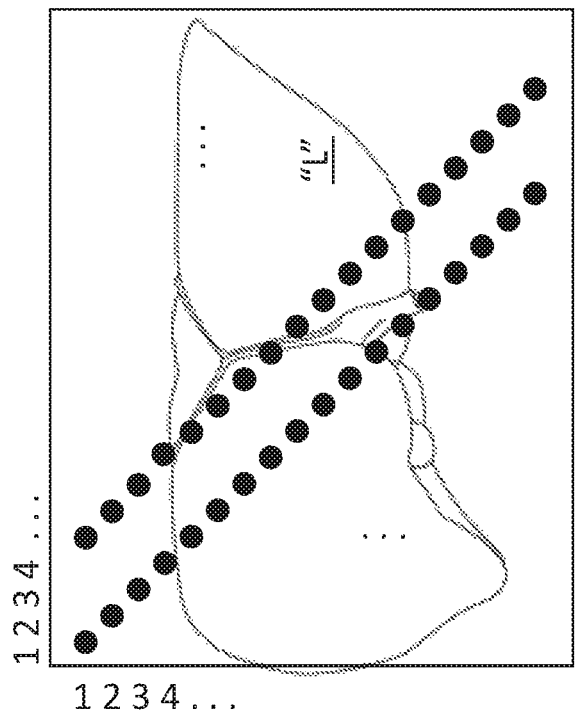
FIGS. 5A and 5B are views of an infrared image captured and segmented according to embodiments of the disclosure.
Figure 5A:
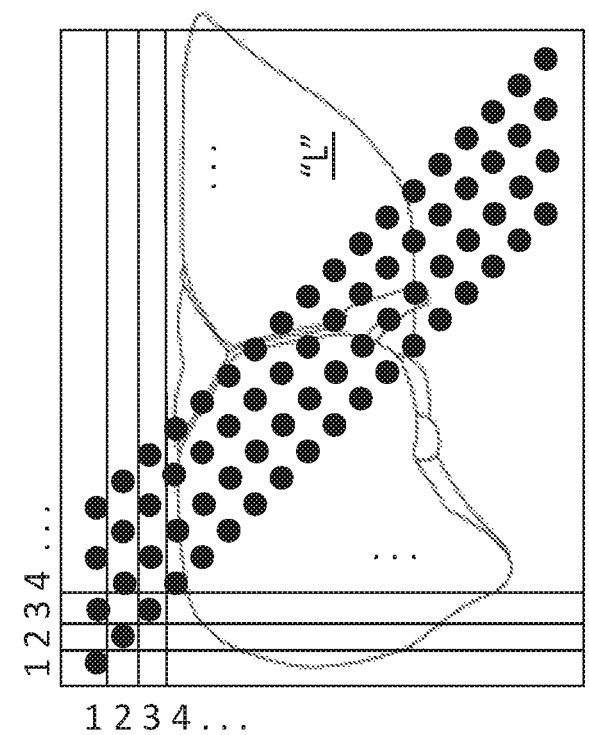

As outlined in the flowchart of FIG. 3A, as the endoscope 200 is advanced toward or otherwise positioned about a target within the patient "P" (e.g., either the interior or the exterior of a liver, prostate, lung, etc.), light is projected away from the distal portion (e.g., the distal surface 204) of the endoscope 200 toward tissue (block 304). More particularly, infrared (IR) light is projected from the laser 210 outward toward one or more anatomical features and surrounding tissue of the patient "F". In embodiments, as shown in FIGS. 5A and 5B, the laser 210 projects a plurality of beams at predetermined distances from one another toward the liver "L" of the patient 102 (FIG. 1). The IR light may also be projected in a predetermined pattern (e.g., a grid or shaped pattern; FIGS. 5A and 5B) or may be projected toward a tissue surface "S" which may include the target, surrounding tissue, other tissue within the body of the patient "P" between an entry point of the endoscope 200 and the target of the patient "P" (FIGS. 5A and 5B), and the like. The IR light may be configured to strike the target and surrounding tissue with each projected beam projected at varying distances from one another, to increase or decrease the precision of each image. For example, in embodiments, the IR light may form one or more patterns such as preselected geometric images (e.g., stripes, random or structured placements of dots). Based on the desired level of accuracy, the patterns may be varied in complexity, having greater amounts of angles, positioned closer to one another, etc. Patterns may also be selected to optimize later analysis of the IR light once captured.

Once the IR light contacts the tissue surface "S" of the patient "P", light is reflected from the surface "S" back toward the second camera 212 (block 306). The light may be received as a plurality of points at varying distances from one another. The second camera 212, in response to receiving the light reflected from the surface "S", transmits an image that includes the reflected light as IR image data to the computing device 400. The computing device 400 stores the IR image data in the memory 402 of the computing device 400, and may store the IR image data in any suitable data structure such as a 2D array, 3D model, etc. For purposes of clarity, storage and analysis of the IR image data will be referred to as a 2D array of distance measurements calculated based on the received IR image data by the computing device 400.

The corresponding distances associated with the IR image data (e.g., the distance at each point where IR light is sensed by the second camera 212) are stored in the memory 402 for association later with a portion of an optical image. In embodiments, an intra-operative 3D model is generated based on the distance measurements captured in the IR image data. After generation of the intra-operative 3D model based on the distance measurements, the intra-operative 3D model may be matched with a portion of a pre-operative 3D model and/or a pre-operative image data (e.g., points contained, or otherwise associated with the pre-operative 3D model). Matching may occur by identifying certain fiducial markers in both the pre-operative 3D model and the intra-operative 3D model and, based on the matching, the pre-operative 3D model and the intra-operative 3D model may be aligned or otherwise associated with one another.

Once the IR image data is captured (see block 306), the laser 210 stops projecting IR light toward the surface "S". After the IR light is no longer transmitted toward the surface "S", the light source 208 projects optical light (e.g., visible light) toward the surface "S" of the patient "P" (block 308). Similar in many respects to the projection and capture of IR light described at blocks 304 and 306, once the optical light contacts the tissue surface "S" of the patient "P", light is reflected from the surface "S" toward the optical camera 206 (block 310). The optical camera 206, in response to receiving the light reflected from the surface "S", transmits the 2D image data to the computing device 400 including the reflected light, the image data referred to as optical image data. The computing device 400 stores the optical image data in the memory 402 of the computing device 400.

The IR image data and optical image data, once captured by the second camera 212 and optical camera 206, respectively, are associated in the memory 402 of the computing device 400 (block 312). More particularly, the computing device 400 generates a 3D model (e.g., the intra-operative 3D model), or a rendering of the 3D model for display on a 2D display, based on the calculated distances of each point in the IR image data and stores the 3D model in the memory 402. The 3D model generated from the IR image data may be stored in the memory 402 in any suitable data structure (e.g., a 2D array of distances from a common plane or a 3D array of points).

The computing device 400 (FIG. 6) generates an intra-operative 3D image based on the association of the IR image data and the optical image data (block 314). More particularly, the computing device 400 maps the optical image data to corresponding points in the 3D model. These points may be mapped by aligning the optical image data with the IR image data (e.g., adjusting the pixels to account for the spatial difference between the optical camera 206 and the second camera 212) and, once aligned, associating the optical image data with the IR image data. For example, when the optical image data is captured as a 2D array of points, the 2D array of points may be advanced or otherwise projected toward the 3D model, with each corresponding point of the 3D model (along the surface of the objects contained therein) associated with the point in the 2D array from the optical image data. Each point may include image data such as color value, luminance, chrominance, brightness, etc. As subsequently captured optical image data is mapped to the 3D model, the earlier-captured optical image data may be compared to the most-recently captured optical image data and updated as is necessary. Once the optical image data is mapped to the IR image data, the computing device 400 may generate the intra-operative 3D model (or, where a 2D display is available, a 2D rendering of an intra-operative 3D image) to be displayed on the display 406 of the computing device 400 based on the mapping of the optical image data to the IR image data. In embodiments, once the intra-operative 3D model and/or the intra-operative 3D image is generated, the computing device 400 causes the output module 412 to output the 2D and/or 3D image (block 316).

In embodiments, the generated 3D image may also be associated with pre-operative 3D models generated from pre-operative image data (block 318). More particularly, the application 416, during execution, may cause the computing device 400 to store the image data associated with the generated 3D image at a corresponding location in the 3D model. This association may enable the computing device 400 to update images generated during EM navigation, or display the intra-operative 3D model (in embodiments, the pre-operative 3D model) generated during planning or review phases of surgical procedures.

It will be understood that when the intra-operative 3D image is generated, the position of the endoscope 200 determined by EM tracking modules (e.g., EM tracking module 724, FIG. 9) may be matched to a corresponding position in the intra-operative 3D image. Based on this matching, the computing device 400 may superimpose a visual representation of the endoscope 200 relative to the intra-operative 3D image data. The modified intra-operative 3D image data may subsequently be displayed on the display 406 of the computing device 400. It will also be appreciated that, while IR light is generated and captured (blocks 304 and 306) prior to the generation and capture of optical light (blocks 308 and 310), the order in which these two types of light are generated and captured may be reversed (e.g., optical light may be generated and captured prior to the generation and capture of IR light), while still adhering to the principles of the disclosure.

Simultaneous Intra-Operative Image Capture

In embodiments, as the endoscope 200 is advanced through or otherwise positioned within the body of the patient "P", the endoscope 200 may image one or more areas therein (process 302'). More particularly, the endoscope 200 may receive 2D and/or 3D image data, generate an intra-operative 3D image or intra-operative 3D model, and either display the generated image data on the display 406 of the computing device 400 and/or store the image data in the memory 402 of the computing device 400. In many respects, this imaging technique may be similar to imaging performed during performance of process 302 (FIG. 3A). In embodiments, the image data may be associated with the pre-operative 3D model generated based on the pre-operative image data of the patient "P". It will be understood that the actions performed by the endoscope 200 may be caused by executing instructions (e.g., the application 416) on the processor 404 or by a local control circuitry disposed, or otherwise in electrical communication with, the various components of the endoscope 200.

As outlined in the flowchart of FIG. 3B, as the endoscope 200 is advanced toward or otherwise positioned about a target within the patient "P", light is projected away from the distal portion (e.g., the distal surface 204) of the endoscope 200 toward tissue (block 304'). Specifically, both IR light (e.g., a plurality of IR light beams or a large beam of IR light covering an entire viewing window) as well as optical light are projected from the laser 210 and light source 208, respectively. The combined lights are directed toward one or more anatomical features and surrounding tissue of the patient "P". In embodiments, as shown in FIGS. 5A and 5B, the laser 210 may project a plurality of beams at predetermined distances relative to each projected beam. The IR light may also be projected in a predetermined pattern (e.g., a grid or shaped pattern; FIGS. 5A and 5B) or may be projected toward a tissue surface "S" which may include the target, surrounding tissue, or both, as well as other tissue within the body of the patient "P" between an entry point of the endoscope 200 and the target of the patient "P" (FIGS. 5A and 5B). The IR light may be configured to strike the target and surrounding tissue with each projected beam being projected at varying distances from one another, to increase or decrease the precision of each IR image. In embodiments, the optical light may be transmitted at a predetermined frequency such that the optical light does not interfere with the capture of IR light by the second camera 212.

Once the IR light and optical light contact the tissue surface "S" of the patient "P", light and optical light are reflected from the surface "S" back toward the optical camera 206 and second camera 212. The optical camera captures and transmits the reflected optical light to the computing device 400 and the second camera captures the reflected IR light to the computing device 400 (block 306'). Once captured, process 302' continues to blocks 308'-310', and optionally to block 312'. Blocks 308'-312' may be performed in a manner similar to blocks 412-416, respectively, and as such their detailed description will be omitted for purposes of clarity.

As outlined in the flowchart of FIG. 3C, optionally, the IR image data, optical image data, intra-operative 3D model generated based on the IR image data and the optical image data, or any combination thereof, may be stored in the memory 402 for later recall. In addition to the display of the intra-operative 3D model (or, in embodiments intra-operative image data) on the display (blocks 316 or 312'; see FIG. 4), the computing device 400 may associate or otherwise update the pre-operative 3D model based on the intra-operative 3D model (block 318). Specifically, the image data associated with the intra-operative 3D model may be matched with a corresponding location in the pre-operative 3D model. The intra-operative 3D model may be compared to the pre-operative 3D model and, based on the comparison, the pre-operative 3D model may be updated to more accurately reflect the environment during navigation of the endoscope 200. For example, if a clinician cut, or otherwise caused tissue to be changed since the pre-operative 3D model was generated, the computing device 400 may update the pre-operative 3D model to reflect the change in tissue of the patient "P" when displaying the pre-operative 3D model during navigation or otherwise. The update may be based on comparing the generated intra-operative 3D model with the pre-operative 3D model of the patient. In embodiments, the computing device 400 may update the navigational pathway (block 320) displayed on the display 406 to enable the clinician to navigate through the body of the patient "P", the update based on the association of the intra-operative 3D model and the pre-operative 3D model (see block 318).

If the computing device 400 determines that the intra-operative 3D model is generated (processes 302 or 302') in connection with the aid of surgical navigation (block 322, see process 602), the computing device 400 causes the display to display an updated navigational screen (explained in greater detail below), including an updated navigational view and updated trajectory (block 324). Alternatively, if the intra-operative 3D model is generated (processes 302 or 302') apart from a navigational procedure, the computing device 400 determines if imaging is occurring in interleave mode ("YES" at block 326) or in simultaneous mode ("NO" at block 326) and reiterates the imaging process (returning to block 304 or block 304', respectively). It will be understood that processes 302 and 302' describe imaging with respect to a single instance (e.g., imaging one time) that these may be repeated continuously so as to create a video stream of intra-operative 3D images.

While the systems and methods described herein refer to the use of IR light to determine distance and optical light to capture optical images for subsequent analysis and display, it will be understood by one skilled in the art that the use of IR light and optical light may be interchanged. More particularly, the light pattern displayed at block 304 or 304' may be projected by the light source 208 and the light used to illuminate the entire surgical space may be projected by the laser 210. It will be understood that both the IR light and the optical light may be received by multiple sensors, to enable stereoscopic imaging of the reflected light by the respective sensors configured to capture the light.

Figure 4:
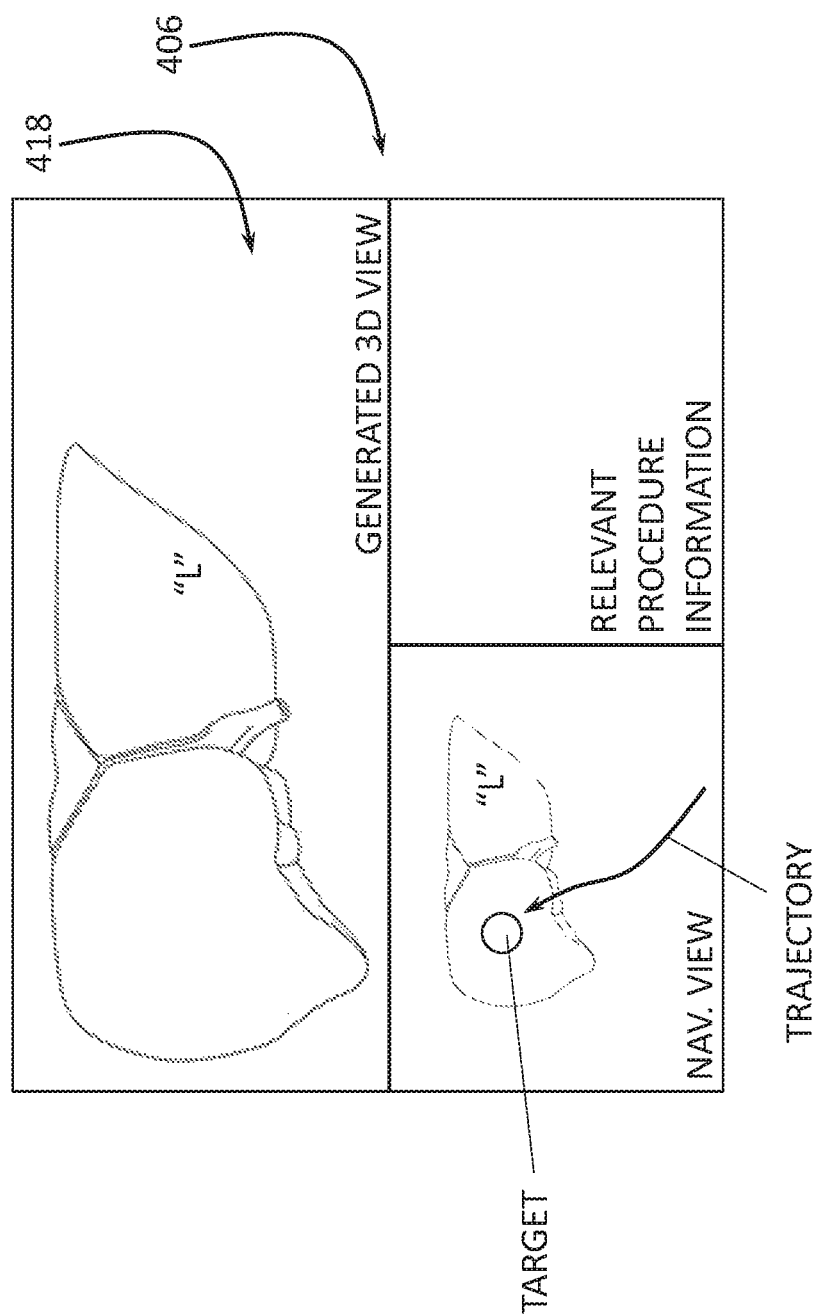
FIG. 4 is a view of a graphical user interface showing an intra-operative 3D model, according to embodiments of the disclosure.

FIG. 4 illustrates a view of a GUI 418 that may be displayed during the performance of process 302, 302'. FIG. 4 includes a display 406 illustrating on a portion thereof the intra-operative 3D model generated based on the IR image data and optical image data sensed during processes 302, 302'. The display 406 also includes, on a separate portion thereof, an illustration of the pre-operative 3D model and trajectory generated during optional navigation of the endoscope 200. Further, optional procedural data may be displayed via the GUI 418 such as, without limitation, the state of the patient "P" during the surgical procedure (e.g., heart rate, blood pressure, etc.), the state of the surgical devices (e.g., operative, engaged, in error), etc. As noted above, in embodiments a visual representation of the endoscope 200 may be matched relative to the displayed intra-operative 3D model and overlaid onto the displayed 3D model based on the matching.

FIG. 6 illustrates a simplified block diagram of a computing device 400. The computing device 400 may include a memory 402, a processor 404, a display 406, a network interface 408, an input device 410, and/or an output module 412. The memory 402 may store the application 416 and/or image data 414. The application 416 (which may be a set of executable instructions) may, when executed by the processor 404, cause the display 406 to present a graphical user interface (GUI) based on GUI instructions 418. The application 416 may also provide the interface between the endoscope 200 and the computing device 400.

The memory 402 may include any non-transitory computer-readable storage media for storing data and/or software (instructions) executable by the processor 404 and which controls the operation of the computing device 400 and/or various components of the endoscope 200, when in communication with the endoscope 200 (e.g., with the optical camera 206, light source, 208, laser 210, second camera 212, etc.). In an embodiment, the memory 402 may include one or more solid-state storage devices such as flash memory chips. Alternatively or in addition to the one or more solid-state storage devices, the memory 402 may include one or more mass storage devices connected to the processor 404 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 404. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by the computing device 400.

The network interface 408 may be configured to connect to a network such as a local area network (LAN) consisting of a wired network and/or a wireless network, a wide area network (WAN), a wireless mobile network, a Bluetooth network, and/or the Internet. The input device 410 may be any device by means of which a user may interact with the computing device 400, such as, for example, a mouse, keyboard, foot pedal, touch screen, and/or voice interface. The output module 412 may include any connectivity port or bus, such as, for example, parallel ports, serial ports, universal serial busses (USB), or any other similar connectivity port known to those skilled in the art.

Planning

An optional planning phase (process 502, including blocks 504-514) which includes various steps performed prior to placing the patient "P" on the operating table 702 (see, e.g., FIG. 9) for a given diagnostic and/or treatment procedures. Initially, the patient "P" (FIG. 9) may be imaged using any suitable imaging device (not shown) to capture pre-operative scan data or pre-operative image data such as the pre-operative 2D and/or 3D image data discussed above. Once the pre-operative 2D and/or 3D image data (referred to throughout the disclosure as pre-operative image data) is obtained, a pre-operative 3D model may be generated. It will be understood that the pre-operative image data may be associated with multiple pre-operative scans. Additionally, the pre-operative image data may be selected from among multiple scans of the same region, with the most recent scan being selected for use. The pre-operative image data may be received in, or converted to, a uniform data format, such as the digital imaging and communications in medicine (DICOM) standard. For example, the pre-operative image data may include image data from a CT scan, a CBCT scan, an MRI scan, a PET scan, an X-ray scan, and the like (block 504).

The computing device 400 processes the pre-operative image data and/or the pre-operative 3D model to identify one or more anatomical structures (e.g., liver, lung, target tissue, tumor, etc.) from the pre-operative image data (block 506). For example, the computing device 400 may identify the liver of the patient "P", as well as potential targets (e.g., lesions, known structures, etc.) thereon. While discussion will generally refer to the processing of the image data associated with the liver of the patient "P", it will be understood that the computing device 400 may identify any known anatomical feature of the patient "P" including, without limitation, one or more lumens of the vascular system, one or more lymph nodes and/or ducts of the lymphatic system, other organs (e.g., the exterior or extents of the surface of any particular organ, or corresponding internal structures thereof), markers, cysts, lesions, or other aberrant structures captured by the pre-operative scan. Processing of the pre-operative image data and/or pre-operative 3D model may include automatic or user-assisted image analysis to identify the anatomical features in the pre-operative image data.

Once the pre-operative image data is received by the computing device 400, an application 416 executed on the processor 404 from the memory 402 of the computing device 400 generates the pre-operative 3D model of the surgical site and, more particularly, of the anatomical features disposed therein (block 508). The pre-operative 3D model includes data which may be subsequently analyzed by the application 416 and displayed on the display 406 of the computing device 400. For example, the data may include 2D and/or 3D graphical representations of the surgical site (e.g., such as the liver of the patient) and may show the locations of features of the anatomical features disposed therein (e.g., the target areas of a lung). The computing device 400 may further label one or more of the identified features such as the elements and sub-elements of one or more organs (block 510).

A target (e.g., a tumor, lesion, position along an organ, etc.) may be selected to which one or more endoscopes 200 are to be navigated toward (block 512). For example, the target may be selected from the structures identified in the pre-operative image data and/or the generated pre-operative 3D model (see block 506). Additionally, or alternatively, the target may be selected manually (e.g., the clinician may review the pre-operative image data and determine a particular region within or along the tissue of the patient "P" to navigate the endoscope 200 toward). In embodiments, the computing device 400 may highlight (or in some other way display) one or more areas as potential lesions and/or tumors detected via image analysis of the pre-operative 3D model and/or the pre-operative image data for clinician review. The clinician may then confirm whether the highlighted areas are targets to be visited during a surgical procedure and provide input to the computing device 400 to mark the confirmed lesions as targets in the pre-operative 3D model. The clinician may also select one or more lesions and/or targets by viewing the pre-operative image data and/or the pre-operative 3D model (block 512). For example, by using the input device 410 and the display 406 of the computing device 400, the clinician may view the pre-operative image data and/or the pre-operative 3D model and identify one or more lesions and/or targets along a specified area within the pre-operative image data or 3D model. The clinician may also select and/or mark various areas of the anatomical features captured within the pre-operative 3D model as requiring diagnosis and/or treatment.

Once the target(s) are selected, the computing device 400 determines a pathway to the target(s) (block 514). More particularly, the computing device 400 may identify a trajectory along which the endoscope 200 may be translated to reach the targets. For example, the computing device 400 may determine a way through the tissue of the patient "P" toward the liver via an incision along the surface of the body of the patient "P". The computing device 400 may select the way through the tissue, or the "path", in order to minimize the travel distance through the body of the patient "P", reduce the chance for potential injury, etc. In embodiments, during lung navigation procedures, the computing device 400 determines a pathway from the mouth or nose of the patient "P" through the luminal network of the patient "P", such as through the airways of the patient "P", to reach the target or targets. Where multiple targets exist and are selected within the pre-operative image data, a plurality of pathways to the target or targets may be identified. Additionally, the computing device 400 may automatically, or with input from the clinician, generate a diagnosis and/or treatment plan based on the identified structures, selected targets, and/or identified pathways. As will be appreciated by those skilled in the art, this diagnosis and/or treatment plan generation may also occur prior to the generation of the pre-operative 3D model by simply viewing the pre-operative image data.

EM Navigation

In embodiments, the endoscope 200 may operate in conjunction with a catheter guide assembly (see, e.g., FIG. 9). The catheter guide assembly may be paired or otherwise configured to control operation of the endoscope 200 during surgical procedures while the endoscope 200 is disposed within the catheter guide assembly.

A six degrees-of-freedom EM tracking system 708 may be used to perform navigation, although it is contemplated that the principles described herein may employed with any known navigation systems and methods.

The EM tracking system 708 may be configured to track a position of the endoscope 200 having at least one EM sensor 718 disposed thereon as the endoscope 200 moves relative to the body of the patient. In embodiments, the EM tracking system 708 includes the EM tracking module 724, a plurality of reference sensors 726, and an EM field generator 722. As shown in FIG. 9, the EM field generator 722 is positioned beneath the patient. The EM field generator 722, as well as the plurality of reference sensors 726, are interconnected with the EM tracking module 724, which derives the location of each reference sensor 726 in the six-degrees-of-freedom. One or more of the reference sensors 726 are placed on or attached to the chest of the patient. The six-degrees-of-freedom coordinates of the reference sensors 726 are sent as data to the computing device 400, which includes an executable set of instructions or application 216 (FIG. 2) that processes data received from the reference sensors 726 to calculate a patient coordinate frame of reference.

The computing device 400 (FIG. 6) includes hardware and/or software, such as the application 416 to facilitate the various phases of surgical procedures. For example, the computing device 400 may use radiographic image data acquired from a CT scan, cone beam computed tomography (CBCT) scan, magnetic resonance imaging (MRI scan, positron emission tomography (PET) scan, X-ray scan, and/or any other suitable imaging modality to generate and display a pre-operative 3D model of certain elements and sub-elements of the anatomical features of the patient, identify a target on the radiographic image data and/or the pre-operative 3D model (automatically, semi-automatically, or manually), and enable the determination and selection of a path through the patient toward the target. During operation, the pre-operative 3D model may be presented on a display device or display 406 associated with the computing device 400, or in any other suitable fashion.

Various generated views of the pre-operative 3D model may be displayed via the display 406 (FIG. 6). While displayed, a clinician may manipulate the displayed pre-operative 3D model via an input device 410 (e.g., a mouse, keyboard, or touch screen (not explicitly shown)), to identify one or more targets. As noted above, targets may be one or more areas of an anatomical feature (e.g., a liver, lung, prostate, etc.), lesions or lymph nodes, a surgical site where treatment is to be performed or other known areas of a patient that require treatment. In embodiments, the pre-operative 3D model may include, among other things, a model anatomical feature corresponding to the actual anatomical features of a patient (e.g., a model may stand in or otherwise be substituted for the pre-operative 3D model), and illustrate the various elements of the anatomical feature (e.g., the shape, structure, etc. of the target tissue) of the patient "P".

Pre-operative 3D models may include lesions, markers, blood vessels, vascular structures, lymphatic structures (e.g., lymph nodes), organs, other physiological structures, and/or a 3D rendering of the pleural surfaces and fissures of the lungs of the patient. Some or all of the aforementioned elements may be selectively displayed, such that the clinician may choose which elements should be displayed when viewing the 3D model. Further, as described below, one or more 3D renderings may be generated based on the pre-operative 3D model and/or an intra-operative 3D model generated prior to or during surgical procedures.

During a procedure, the EM sensor 718 of the endoscope 200, in conjunction with the EM tracking system 708, may be used to track and determine the position of the endoscope 200 while advanced through and/or about the body of the patient "P". Tracking may occur in connection with a pre-planned navigation plan. As an initial step of the procedure, the 3D model is registered with certain anatomical features of the patient (e.g., the extents of an organ, the bronchial structures of a lung, etc.). One potential method of registration involves navigating the endoscope 200 into known regions of the body of the patient. The position of the endoscope 200 is tracked by the EM tracking system 708 during this registration phase, and the 3D model is iteratively updated based on the tracked position of the endoscope 200 within the actual body and, in certain cases, anatomical features of the patient. While the registration process may focus on aligning the organs of a patient and verifying the continued accuracy of the pre-operative 3D model, registration may similarly be performed within an organ (e.g., within the airways of the patient).

As the endoscope 200 is advanced or navigated through a body cavity or internal to an organ, images projected to the clinician via a display may be derived from any combination of preoperative imaging data, as well as 2D or 3D imaging data obtained while the distal portion of the endoscope 200 was positioned in a similar position relative to the body or organ prior (e.g., during an earlier surgical procedure). As the images including the previously obtained image data are displayed, the computing device 400 may update the displayed images based on identifying the position of the anatomical features (e.g., by matching natural fiducial markers with fiducial markers in the preoperative image data). As a result of this updating of the preoperative image data stored in the memory 402 of the computing device 400, the virtual images displayed to assist during the navigation of the endoscope 200 may be reconstructed to reflect any changes between the preoperative image data and instantly-captured image data. This intra-operative updating enables the computing device 400 to provide a continuous image stream that is responsive to shifts in natural fiducial markers. Additionally, should the display of the real time images of the environment which the endoscope 200 is disposed in be delayed, obstructed, etc., the updated preoperative image data may be displayed to compensate for such distortions.

The computing device 400 may update and/or enhance the pre-operative 3D model based on the registration of the endoscope 200 relative to the patient "P" to the pre-operative 3D model. The computing device 400 may then generate a plan for imaging the organ(s) for the subject surgical procedure. More particularly, the computing device 400 may determine one or more trajectories through the patient "P", either along anatomical features contained in an intra-operative 3D model.

An optional EM navigation phase (process 602, including blocks 604-616) may be performed, either in addition to or during an optical imaging phase (process 302, 302'). Those skilled in the art will recognize that the planning phase may occur separate and apart from the navigation phase (e.g., at some date or time prior to the performance of the surgical procedure). The navigation phase may include the navigation of the endoscope 200 of the EMN system 700 toward the identified anatomical structures and/or targets (see block 432) via the determined pathway (see block 540). In embodiments, the EM navigation phase may occur in connection with navigation via one or more predetermined paths not specific to the patient "P". Further, while EM navigation will be described with regard to a predetermined path toward the one or more identified targets, it will be understood that, in embodiments, the computing device 400 may, independent of any possible navigation phase, perform image generation based on the intra-operative image data obtained from the endoscope 200 during the surgical procedure.

Initially, during EM navigation, a navigation plan is selected and loaded for display of the target and the pathway on the 3D model (block 604). In embodiments, the computing device 400 may cause a display device, such as display 406, to display the pre-operative 3D model with the target and the pathway indicated thereon. The EM field generator 722 of the EM tracking system 708 generates an EM field about the body of the patient "P", and in particular about the chest of the patient "P" as illustrated in FIG. 9 (block 606). The EM tracking system 708 then detects a position of the EM sensor 718 of the endoscope 200 in the EM field (block 608), and based on the position of the EM sensor 718, the EM tracking system 708 provides EM tracking data to the computing device 400 indicative of the position of the EM sensor 718, and by extension, the endoscope 200.

Optionally, once the EM tracking data is received, an intra-operative 3D model may be generated based on the location of the endoscope 200 relative to the body of the patient "P", as well as earlier-captured pre-operative image data, described above (block 610). Alternatively, or additionally, optical image data and/or intra-operative 3D image data may be compared to the pre-operative 3D model to determine the position of the endoscope 200. As the endoscope 200 is advanced through the body of the patient "P", 2D and/or 3D image data may be registered with the pre-operative 3D model. This registration may enable the computing device 400 to update the pre-operative 3D model (referred to during a surgical procedure as an intra-operative 3D model) to enable more realistic visualization of the anatomical features in proximity to the endoscope 200. In embodiments, the pre-operative image data is obtained in close temporal relation to the surgical procedure (e.g., prior to the procedure) and, as such, the pre-operative 3D model may not require registration with the patient "P". In such embodiments, the pre-operative 3D model is aligned with the body of the patient "P" on the operating table 702. Alignment may be achieved by analyzing the position of the reference sensors 726 or other markers placed about the body of the patient "P" prior to obtaining the pre-operative image data. It will be understood that the pre-operative 3D model may not be updated, and as such, subsequent reference to an intra-operative 3D model may refer to the pre-operative 3D model.

After the intra-operative 3D model is registered and/or aligned with the body of the patient "P", the computing device 400 determines a position of the endoscope 200 based on the EM tracking data received from the EM tracking system (block 612). The computing device 400 displays the tracked position of the endoscope 200 on the intra-operative 3D model of the patient "P", thereby indicating the position of the endoscope 200 relative to the anatomical features of the patient "P" (block 614). Additionally, or alternatively, the endoscope 200 may collect 2D and 3D image data and generate inter-operative image data (e.g., interleave mode (see process 302), or simultaneous mode (see process 302')) without registering the endoscope 200 with the patient "P". This generated 3D image data may also be mapped to the intra-operative 3D model to update the intra-operative 3D model.

In embodiments, the computing device 400 causes the display 406 to display the tracked position of the endoscope 200 on the intra-operative 3D model while displayed on the display 406. In embodiments, the computing device 400 may also cause the display 406 to display a virtual representation of the endoscope 200 (or any suitable portion thereof) relative to the anatomical features of the patient "P" along the intra-operative 3D model. This visual representation is based on the known position of the endoscope 200 derived by the EM tracking module 724 relative to the patient "P". The display 406 may illustrate additional position information, including a direction in which the endoscope 200 is directed, as well as the position and orientation (hereinafter "pose") of the endoscope 200 relative to the patient "P".

During EM navigation, the computing device 400 determines whether the endoscope 200 reached the target (block 616). For example, the computing device 400 may determine whether the EM tracking data received from the EM tracking module 724 indicates that the EM sensor 718 of the endoscope 200 is proximate to the position of the target (e.g., whether the EM sensor 718 is within a predetermined distance of the target). If the computing device 400 determines that the endoscope 200 has not reached the target ("NO" at block 616), process 600 returns to block 612. If the computing device 400 determines that the endoscope 200 reached the target ("YES" at block 616), process 600 continues to block 608.

FIG. 9 illustrates larger surgical systems (e.g., lung navigation systems) which may be employed in connection with the above-described systems and methods. In these embodiments, the pre-procedural images may image the pathways of a bronchial, vascular, and/or lymphatic tree structure, growths disposed thereabout or therein, as well as sub-anatomical features such as blood vessels. The pre-procedural imaging may capture information associated with pleural surfaces and fissures located within a patient (e.g., within the lungs of the patient). These pre-operative 3D models may be generated via the computing device 400 of FIG. 3 in a manner similar to that described above with respect to the pre-procedural 3D models. Such software applications may, for example, generate the visual representation of the anatomical features of the patient based on radiographically obtained images, such as computed tomography (CT) images, magnetic resonance imaging (MRI) images, positron emission tomography (PET) images, X-ray images, cone-beam computed tomography (CBCT) images, and/or any other applicable imaging modality. The images may be processed to create a volume of image data of the chest, abdomen, etc. of the patient. Based on the volume of image data, a 3D model of the anatomical feature of the patient is generated, referred to as a pre-operative 3D model. The image data and/or pre-operative 3D model may further be processed to identify one or more targets, such as tumors, lesions, or other aberrant structures, in the area of the patient modeled. For example, the application may identify the locations of growths along the liver, prostate, lungs, etc. of the patient. Similarly, the application may identify the locations of lumens, such as airways, blood vessels, and/or lymphatic structures from the radiographic image data, and further determine the locations of one or more diagnostic or treatment targets.

In embodiments, the application may then receive or load pre-existing pre-operative 3D models such as, without limitation, pre-scanned models of the liver, prostate, etc., of a prototypical patient. Similarly, the application may receive or load a model lymph node map, such as the International Association for the Study of Lung Cancer (IASLC) map, which includes the locations of lymph nodes in a model of the body of a typical patient. Thereafter, the application may fit the pre-existing 3D model to the pre-operative 3D model to align the pre-existing 3D model with the body of the patient and, more particularly, the identified anatomical structures of the patient to identify the structures contained therein. In embodiments where imaging is to be performed in the lungs of the patient, one or more lymphatic tree maps of the lymphatic system of the patient may be generated based on the model lymph node map fitted on to the 3D model. The generated pre-operative 3D model may further be fitted and/or updated based on known locations of anatomical features of the patient.

The 3D model, radiographic image data, and/or lymphatic tree map may then be displayed to, and viewed by, clinicians during the planning phase or surgical phase of a surgical procedure, such as during a diagnostic or treatment procedure. For example, a clinician may identify one or more areas of concern to be visited during a subsequent biopsy, ablation, radiation, resection, surgical, or other such interventional procedure. The clinicians may review the 3D model, radiographic image data, and/or the lymphatic tree map to identify one or more structures such as organs (e.g., a liver, lung, prostate, etc.), lymph nodes, lesions, and/or other targets for diagnosis and/or sampling. The application may then determine a path to the identified structures to assist a clinician with navigating with one or more surgical tools through the body of the patient to the targets or anatomical features, as further described below. Navigation may occur through an incision made along the body of the patient (e.g., during laparoscopic interventions, see FIG. 1), through the mouth and/or nose of the patient (for bronchial intervention), or any other known manner by which an endoscope may be introduced into the body of a patient.

In embodiments, an intra-operative 3D model may be generated and registered or associated with the pre-operative 3D model. The association of the image data and the pre-operative 3D model, radiographic image data, and/or lymphatic tree map during registration may be based on the known position of the surgical tool relative to the pre-operative 3D model identified when the intra-operative image data was obtained. The 3D rendering and/or the intra-operative 3D model, as well as the association of the intra-operative 3D model to the body of the patient may then be updated and/or augmented. The 3D rendering, the intra-operative 3D model, the pre-operative 3D model, and/or a fusion thereof may then be displayed during a subsequent diagnostic or treatment procedures. EMN systems such as the ELECTROMAGNETIC NAVIGATION BRONCHOSCOPY (ENB) system currently sold by Covidien LP, a division of Medtronic PLC are contemplated as incorporating the described systems and methods.

FIG. 9 illustrates an EMN system 700 suitable for implementing methods for performing treatment procedures is illustrated. As shown the EMN system 700 is used to perform one or more treatment procedures on a patient supported on an operating table 702. In this regard, the EMN system 700 generally includes a bronchoscope 704, monitoring equipment 706, an EM tracking system 708, an endoscope 200 (FIG. 2), and a computing device 400 (FIG. 3).

The bronchoscope 704 is configured for insertion through the mouth and/or nose of the patient to gain access to the airways of the patient. The bronchoscope 704 includes a light source configured for selective engagement (e.g., in response to signals received by the computing device 400) and a video imaging system (both of which are not explicitly shown). The video imaging system of the bronchoscope 704 includes at least one optical sensor (such as a camera sensor) which is in operative communication with the monitoring equipment 706, for example, a video display, for displaying the video images received from the video imaging system of the bronchoscope 704. In embodiments, the bronchoscope 704 includes an ultrasound sensor (not shown). The bronchoscope 704 may operate in conjunction with a catheter guide assembly 710. The catheter guide assembly 710 includes an extended working channel (EWC) 712 configured for insertion through a working channel of the bronchoscope 704 into the airways of the patient (although the catheter guide assembly 710 may also be used without the bronchoscope 704). The catheter guide assembly 710 further includes a handle 714 connected to the EWC 712, the handle 714 being configured for manipulation (e.g., rotation, compression, etc.) to steer or guide the EWC 712 during surgical procedures. During operation of the catheter guide assembly 710, the LG 716, including an EM sensor 718 (similar to EM sensor 214, see FIG. 2), is inserted into the EWC 712 and locked into position such that the EM sensor 718 extends a desired distance beyond a distal portion 720 of the EWC 712. The location of the EM sensor 718, and by extension the distal portion 720 of the EWC 712 (which may, in embodiments, refer specifically to the distal tip of the EWC 712), within an EM field generated by an EM field generator 722 may be derived by an EM tracking module 724 and the computing device 400.

The EM tracking system 708 may be configured for use with the catheter guide assembly 710 to track a position of the EM sensor 718 as it moves in conjunction with the EWC 712 through the body of the patient, in embodiments, the EM tracking system 708 includes the EM tracking module 724, a plurality of reference sensors 726, and an EM field generator 722. As shown in FIG. 1, the EM field generator 722 is positioned beneath the patient. The EM field generator 722, as well as the plurality of reference sensors 726, are interconnected with the EM tracking module 724, which derives the location of each reference sensor 726 in the six-degrees-of-freedom. One or more of the reference sensors 726 are placed on or attached to the chest of the patient. The six-degrees-of-freedom coordinates of the reference sensors 726 are sent as data to the computing device 400, which includes an application 216, where the data from the reference sensors 726 are used to calculate a patient coordinate frame of reference.

Although the EM sensor 718 is described above as being included in a locatable guide (LG) 716, it is also envisioned that the EM sensor 718 may be embedded or incorporated within a treatment tool, such as an endobronchial ultrasound (EBUS) tool (not shown), an ablation tool 728, or the endoscope 200 (FIG. 1B), as well as diagnostic tools such as camera tools, light sensors, linear ultrasound tools, etc., where the treatment tool may alternatively be utilized for navigation without the need of the LG 716 or the necessary tool exchanges that of the LG 716 requires. The EM sensor 718 may also be embedded or incorporated within the EWC 712, such as at a distal portion of the EWC 712, thereby enabling tracking of the distal portion of the EWC 712 without the need for a separate LG 716. According to embodiments, the ablation tool 728, and endoscope 200 are configured to be insertable into the catheter guide assembly 710 following navigation to a target and removal of the LG 716. The EBUS includes at least one ultrasound sensor configured to capture ultrasound images. The ultrasound sensor may be configured to capture ultrasound image data using various frequencies and/or modes of operation, as will be known to those skilled in the art. One example mode of operation includes Doppler. In embodiments, the EBUS may further include a biopsy tool, such as a needle and/or a brush, which may be used to collect one or more tissue samples from the target during surgical procedures. The EBUS may further include one or more expandable balloons which may be used to lock the position of the EBUS during ultrasound imaging and/or while a biopsy procedure is being performed. In embodiments, the EBUS is configured for use in conjunction with the EM tracking system 708 to facilitate navigation of the EBUS to the target by tracking the position of the EM sensor 718, and by extension the EBUS, as the EBUS is navigated through the airways of the patient and/or during manipulation thereof relative to a target. The EBUS may additionally be coupled to an ultrasound workstation (not shown) and/or the computing device 400 to facilitate capture, processing, and analysis of ultrasound images acquired by the ultrasound sensor. The ablation tool 728 is configured to be operated with a generator 730, such as a radio frequency generator or a microwave generator, and may include any of a variety of ablation tools and/or catheters. In addition to the tools described above and/or in the incorporated documents, those skilled in the art will recognize that other tools, including, for example, RF ablation tools, brachytherapy tools, and others may be similarly deployed and tracked without departing from the scope of the disclosure.

The computing device 400 includes hardware and/or software, such as an application 416, used to facilitate the various phases of an EMN procedure. For example, the computing device 400 utilizes radiographic image data acquired from a CT scan, cone beam computed tomography (CBCT) scan, magnetic resonance imaging (MRI) scan, positron emission tomography (PET) scan, X-ray scan, and/or any other suitable imaging modality to generate and display a 3D model of the airways of a patient, identify a target on the radiographic image data and/or 3D model (automatically, semi-automatically, or manually), and allow for the determination and selection of a pathway through the airways of a patient toward the target. The 3D model may be presented on a display device associated with the computing device 400, or in any other suitable fashion.

Using the computing device 400, various views of the pre-operative 3D model may be displayed to, and manipulated by, a clinician to facilitate identification of a target during surgical procedures. As noted above, the target may be one or more areas of an anatomical feature (e.g., a liver, lung, prostate, etc.), lesions or lymph nodes, a surgical site where treatment is to be performed, and/or a portion of, or an entire lobe, or multiple lobes, of the lungs of a patient that require treatment. The pre-operative 3D model may include, among other things, a model anatomical feature corresponding to the actual anatomical features of a patient, and illustrate the various elements of the anatomical feature (e.g., vascular structure, shape, tissue, etc.) of the patient. Additionally, the pre-operative 3D model may include lesions, markers, blood vessels, and vascular structures, lymph nodes and other lymphatic structures, organs, other physiological structures, and/or a 3D rendering of the pleural surfaces and fissures of the lungs of the patient. Some or all of the aforementioned elements may be selectively displayed, such that the clinician may choose which elements should be displayed when viewing the 3D model. Further, as described below, one or more 3D renderings may be generated based on the pre-operative 3D model and/or an intra-operative 3D model generated prior to or during surgical procedures.

Figure 7:
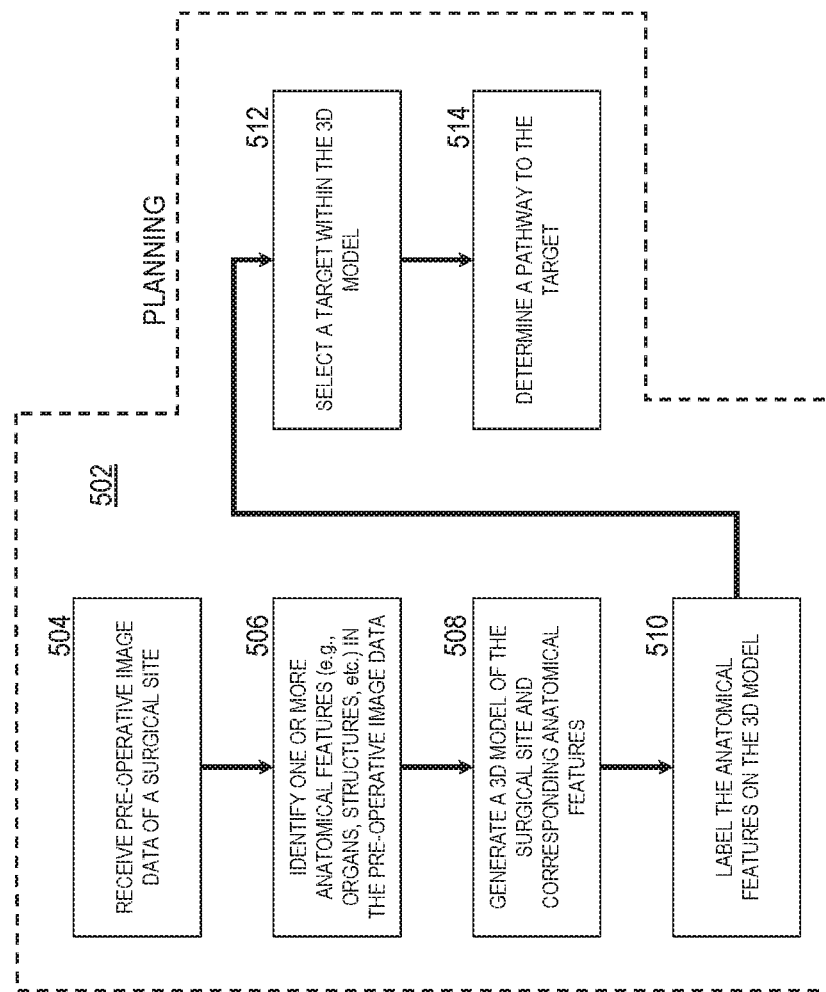
FIG. 7 shows a flowchart of an illustrative optional method for planning a surgical procedure according to embodiments of the disclosure.
Figure 8:
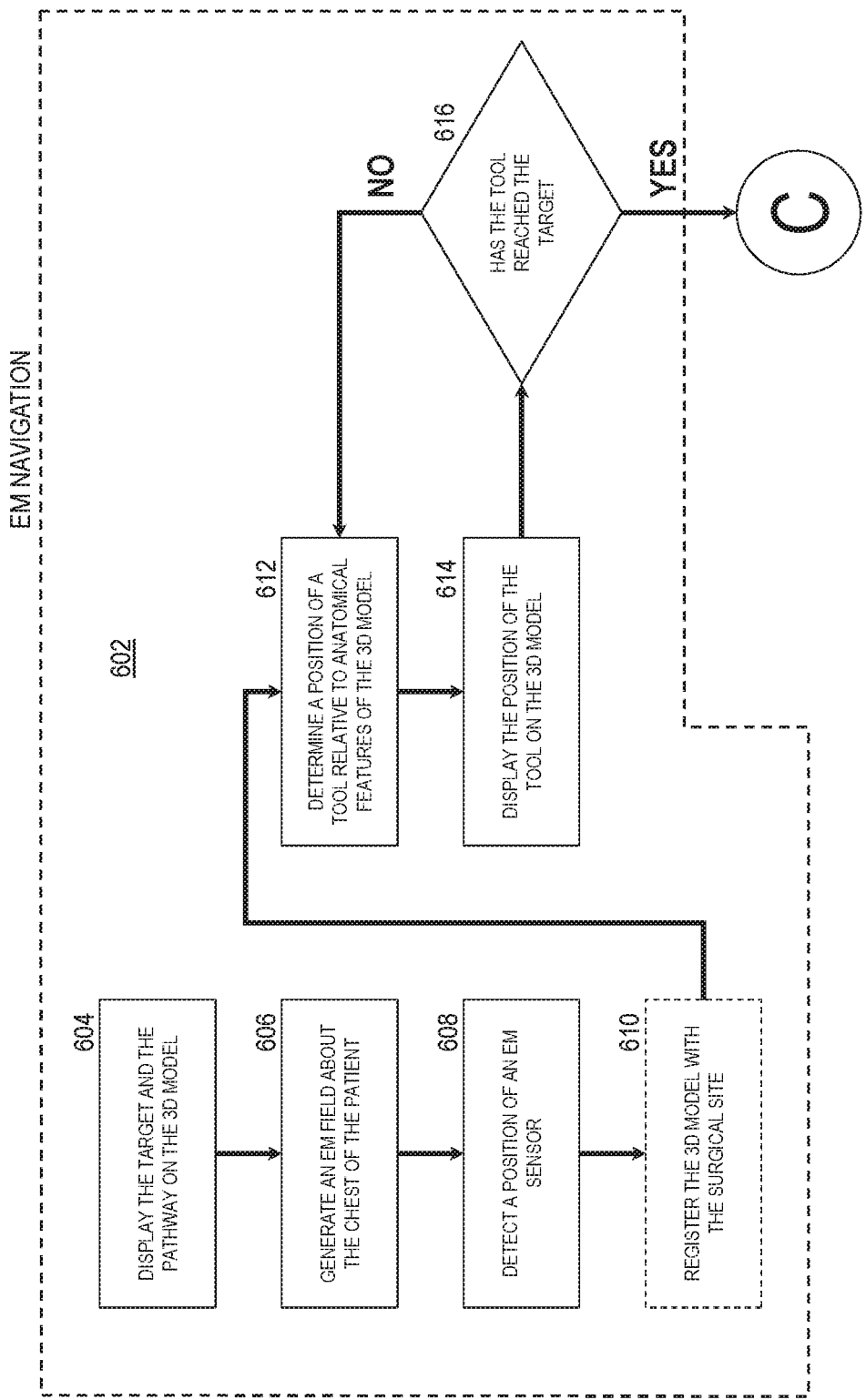
FIG. 8 shows a flowchart of an illustrative optional method for navigating a surgical instrument during a surgical procedure according to embodiments of the disclosure.

During a procedure, the EM sensor 718, in conjunction with the EM tracking system 708, enables tracking of the EM sensor 718 (and thus, the distal portion 720 of the EWC 712, ablation tool 728, or endoscope 200) as EM sensor 718 is advanced through the body of the patient following the pathway planned during the planning phase of the EMN procedure (see FIG. 7). As an initial step of the procedure, the 3D model is registered with certain anatomical features (e.g., the extents of an organ, the bronchial structures of a lung, etc.) of the patient. One potential method of registration involves navigating LG 716 (or another tool including the EM sensor 718) into known regions of the body of the patient. The position of the LG 716 is tracked during this registration phase, and the 3D model is iterative updated based on the tracked position of the locatable guide within the actual body and, in certain cases, anatomical features of the patient. While the registration process may focus on aligning the actual airways of the patient with the airways of the 3D model, registration may also focus on aligning the actual organs of a patient and verifying the continued accuracy of the pre-operative 3D model.

At various times during the procedure, the EBUS may acquire ultrasound image data of various portions of the body of the patient, such as anatomical features, lesions, lymph nodes, and/or other structures. The computing device 400 may then generate the aforementioned intra-operative 3D model and/or intra-operative 3D image data of imaged portions of the anatomical features, lesions, lymph nodes, and/or other structures based on the ultrasound image data. The computing device 400 may then register the intra-operative 3D model to the pre-operative 3D model based on the known position of the EBUS while the ultrasound image data is obtained (based on the EM sensor 718 coupled to the EBUS).

The computing device 400 may then update and/or enhance the pre-operative 3D model and/or intra-operative 3D model based on the ultrasound image data and/or the intra-operative 3D image data. The computing device 400 may further update and/or enhance the registration of the 3D rendering to the 3D model. For example, the ultrasound image data may provide additional clarity and/or identify structures that are not visible in the radiographic image data and/or the 3D model, and the positions of such additional structures may be used to improve the registration of the pre-operative 3D model to the body of the patient. The computing device 400 may then generate a plan for obtaining biopsy samples from one or more of the lesions or lymph nodes of which 3D renderings were generated. It will be understood that the described system of FIG. 7 may be employed according to the methods described with respect to FIGS. 3A-3C.

While detailed embodiments of systems and methods have been described herein, these embodiments are merely examples illustrative of the principles disclosed by the disclosure. Therefore, specific structural and/or functional details disclosed herein are not to be interpreted as limiting, but merely as a basis for the claims and as a representative basis for allowing one skilled in the art to variously employ the disclosure in appropriately detailed structure. While the preceding embodiments are described in terms of imaging anatomical features such as organs (e.g., the liver, lungs, etc.) of a patient, those skilled in the art will realize that the same or similar systems and methods may be used to image areas of the body accessible with an endoscope or other similarly sized surgical instruments. Also, while the use of IR light is discussed, it will be understood that other range finding systems are contemplated such as RADAR, LIDAR, ultrasonic sensors, etc.

While several embodiments of the disclosure are shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of imaging within a body of a patient, the method comprising:
analyzing a first image including reflected grid pattern of IR light captured by an IR camera associated with an endoscope;
analyzing a second image including reflected optical light captured by an optical light camera associated with the endoscope;
associating the first image with the second image;
generating an intra-operative 3D image based on the association of the first image with the second image,
matching the intra-operative 3D image with at least a portion of a pre-operative 3D model based on matching of a natural fiducial appearing in both the intra-operative 3D image and the pre-operative 3D model; and
displaying the intra-operative 3D image and the pre-operative 3D model, wherein, if a portion of the intra-operative 3D image is obstructed or delayed, where there is a delay in processing of the intra-operative image, a corresponding portion of the pre-operative 3D model is substituted.

2. The method according to claim 1, wherein associating the first image and the second image includes mapping the first image to the second image by translating points of the first image to corresponding points of the second image.

3. The method according to claim 1, further comprising projecting a plurality of IR light beams toward at least one anatomical feature of the patient.

4. The method according to claim 3, wherein the plurality of IR light beams are projected toward the at least one anatomical feature in spaced relation relative to one another.

5. The method according to claim 3, wherein the plurality of IR light beams projected toward the at least one anatomical feature are projected in a grid pattern.

6. The method according to claim 1, further comprising determining a plurality of 3D coordinates based on the first image.

7. The method according to claim 6, wherein the generating the intra-operative 3D image is further based on the plurality of 3D coordinates.

8. A system for imaging within a body of a patient, the system comprising an endoscope comprising:
an infrared (IR) light source configured to project a plurality of IR light beams onto at least one anatomical feature in a grid pattern;
an IR camera configured to capture a first image, the first image including a reflection of the plurality of IR light beams;
an optical light source configured to project optical light onto the at least one anatomical feature; and
an optical camera configured to capture a second image, the second image including the at least one anatomical feature illuminated by the optical light source; and
a computing device in communication with the endoscope, the computing device having a processor and a memory storing instructions thereon which, when executed by the processor, cause the computing device to:
associate the first image with the second image;
generate an intra-operative 3D image based on the association of the first image with the second image;
match the intra-operative 3D image with at least a portion of a pre-operative 3D model based on matching of a natural fiducial appearing in both the intra-operative 3D image and the pre-operative 3D model; and
display the matched intra-operative 3D image and pre-operative 3D model, wherein if a portion of the intra-operative 3D image is obstructed or delayed, a corresponding portion of the pre-operative 3D model is displayed.

9. The system according to claim 8, wherein the memory further stores instructions thereon which, when executed by the processor, cause the computing device to:
map the first image to the second image by translating points of the first image to corresponding points of the second image.

10. The system according to claim 8, wherein the memory further stores instructions thereon which, when executed by the processor, cause the computing device to:
determine a plurality of 3D coordinates based on the first image.

11. The system according to claim 10, wherein the memory further stores instructions thereon which, when executed by the processor, cause the computing device to:
  generate the intra-operative 3D image based on the association of the first image with the second image and further based on the plurality of 3D coordinates.

12. The system according to claim 8, wherein the memory further stores instructions thereon which, when executed by the processor, cause the computing device to:
  associate the generated intra-operative 3D image with previously acquired pre-operative images.

13. The system according to claim 12, wherein the memory further stores instructions thereon which, when executed by the processor, cause the computing device to:
  generate a 3D model based on the association of the generated intra-operative 3D image with previously acquired pre-operative images; and display the generated 3D model.

14. A non-transitory computer-readable storage medium encoded with a program that, when executed by a processor, causes the processor to:
  associate a first image of at least one anatomical feature including IR light projected in a grid pattern thereon with a second image of the at least one anatomical feature;
  generate an intra-operative 3D image based on the association of the first image with the second image; and
  match the intra-operative 3D image with at least a portion of a pre-operative 3D model based on matching of a natural fiducial appearing in both the intra-operative 3D image and the pre-operative 3D model; and
  display the intra-operative 3D image and pre-operative 3D model, wherein if a portion of the intra-operative 3D image is obstructed or delayed, a corresponding portion of the pre-operative 3D model is displayed.

15. The non-transitory computer-readable storage medium of claim 14, wherein the program, when executed by the processor, further causes the processor to:
  generate a 3D model based on the association of the generated intra-operative 3D image with the pre-operative 3D model; and
  display the generated 3D model.

16. The non-transitory computer-readable storage medium of claim 14, wherein the program, when executed by the processor, further causes the processor to:
  map the first image to the second image by translating points of the first image to corresponding points of the second image.

17. The non-transitory computer-readable storage medium of claim 15, wherein the program, when executed by the processor, further causes the processor to:
  determine a plurality of 3D coordinates based on the first image.

18. The non-transitory computer-readable storage medium of claim 17, wherein the program, when executed by the processor, further causes the processor to:
  generate the intra-operative 3D image based on the association of the first image with the second image and further based on the plurality of 3D coordinates.

* * * * *